United States Patent
Kato

(10) Patent No.: US 11,198,787 B2
(45) Date of Patent: Dec. 14, 2021

(54) POLYAMIDE RESIN, MOLDED BODY, LAMINATE, MEDICAL DEVICE, AND POLYAMIDE RESIN PRODUCTION METHOD

(71) Applicant: KANEKA CORPORATION, Osaka (JP)

(72) Inventor: Takayuki Kato, Settsu (JP)

(73) Assignee: KANEKA CORPORATION, Osaka (JP)

( * ) Notice: Subject to any disclaimer, the term of this patent is extended or adjusted under 35 U.S.C. 154(b) by 224 days.

(21) Appl. No.: 16/348,045

(22) PCT Filed: Nov. 9, 2017

(86) PCT No.: PCT/JP2017/040479
§ 371 (c)(1),
(2) Date: May 7, 2019

(87) PCT Pub. No.: WO2018/088497
PCT Pub. Date: May 17, 2018

(65) Prior Publication Data
US 2019/0270885 A1 Sep. 5, 2019

(30) Foreign Application Priority Data

Nov. 10, 2016 (JP) .............................. JP2016-220060

(51) Int. Cl.
| | | |
|---|---|---|
| *C08L 77/06* | (2006.01) |
| *C08G 69/40* | (2006.01) |
| *C08G 69/36* | (2006.01) |
| *A61L 29/06* | (2006.01) |
| *B29C 48/00* | (2019.01) |
| *B29K 77/00* | (2006.01) |

(52) U.S. Cl.
CPC .............. *C08L 77/06* (2013.01); *A61L 29/06* (2013.01); *C08G 69/36* (2013.01); *C08G 69/40* (2013.01); *B29C 48/022* (2019.02); *B29K 2077/00* (2013.01); *C08L 2203/02* (2013.01); *C08L 2203/16* (2013.01)

(58) Field of Classification Search
CPC ...................................................... C08L 77/06
See application file for complete search history.

(56) References Cited

U.S. PATENT DOCUMENTS

| | | |
|---|---|---|
| 5,053,484 A | 10/1991 | Speranza et al. |
| 5,744,570 A | 4/1998 | Gebben |
| 2007/0172670 A1* | 7/2007 | Mutsuda ........... B29C 66/91411 428/423.5 |
| 2009/0274913 A1 | 11/2009 | Okushita et al. |
| 2011/0014833 A1 | 1/2011 | Hagiwara et al. |

FOREIGN PATENT DOCUMENTS

| | | |
|---|---|---|
| JP | 59-131628 A | 7/1984 |
| JP | 59-193923 A | 11/1984 |
| JP | 4-227633 A | 8/1992 |
| JP | 9-118750 A | 5/1997 |
| JP | 2001-19763 A | 1/2001 |
| JP | 2011-207935 A | 10/2011 |
| WO | WO 2007/145324 A1 | 12/2007 |
| WO | WO 2009/139087 A1 | 11/2009 |

OTHER PUBLICATIONS

International Search Report issued PCT/JP2017/040479 (PCT/ISA/210), dated Jan. 30, 2018.

* cited by examiner

*Primary Examiner* — Michael F Pepitone
(74) *Attorney, Agent, or Firm* — Birch, Stewart, Kolasch & Birch, LLP

(57) ABSTRACT

A polyamide resin with an excellent balance of mechanical characteristics such as breaking strength and breaking elongation in a solid state, a molded body containing said polyamide resin, a laminate provided with a film or sheet containing said polyamide resin, a medical device provided with the aforementioned molded body and or the aforementioned laminate, and a production method of the aforementioned polyamide resin are provided. The polyamide resin contains units derived from an aliphatic aminocarboxylic acid and corresponding to a hard segment, dicarbonyl units derived from a linear aliphatic dicarboxylic acid, and aliphatic diamino units each having a prescribed structure and containing an ether bond.

14 Claims, No Drawings

POLYAMIDE RESIN, MOLDED BODY, LAMINATE, MEDICAL DEVICE, AND POLYAMIDE RESIN PRODUCTION METHOD

This application is a U.S. National Phase of PCT/JP2017/040479, filed Nov. 9, 2017, and which claims priority under 35 U.S.C. § 119(a) to Application No. 2016-220060 filed in Japan, on Nov. 10, 2016, the entire contents of all of which are expressly incorporated by reference into the present application.

TECHNICAL FIELD

The present invention relates to a polyamide resin, a molded body containing the polyamide resin, a laminate provided with a film or a sheet containing the polyamide resin, a medical device provided with at least one of the molded body and the laminate, an a method for producing the polyamide resin.

BACKGROUND ART

Polyamide resin like polyamide elastomer is a resin compound that is widely used in various fields such as packaging materials for food and the like, members for medical devices, members for electric/precision machine devices, and parts for automobiles. Among them, the parts for medical devices are used as a constitutional part such as a medical tube or catheter balloon. For a use in such members for medical devices, the polyamide elastomer is required to have moldability such as extrusion moldability and blow moldability, which enables fine molding into a desired shape, and dynamic characteristics such as elasticity, breaking elongation, and breaking strength, which enable withstanding of destruction caused by pressure or bending applied during use.

Patent Document 1 discloses a block polyether amide that is obtained by condensation polymerization of a certain polyamide having a carboxy group on both ends, polyoxyalkylene having an amino group on both ends and having an alkylene group containing 3 or more carbon atoms, and a certain diamine. Furthermore, Patent Document 2 discloses polyether amide that is obtained by polycondensation of a polyamide-forming monomer, polyoxyalkylene having an amino group on both ends and having an alkylene group containing 3 or more carbon atoms, a certain diamine, and a certain amount of dicarboxylic acid. The polyether amides described in Patent Documents 1 and 2 are considered to have a certain degree of elasticity and impact resistance. However, with regard to the polyether amides with the component constitution described in Patent Documents 1 and 2, even with a use of the polyether having an alkylene group containing 3 or more carbon atoms, mechanical strength such as elasticity, breaking elongation, and breaking strength is insufficient, and thus is required.

Patent Document 3 discloses a polyamide elastomer that is obtained by polymerization of (A) a polyamide-forming monomer selected from certain aminocarboxylic acid compounds and certain lactam compounds, (B) at least one diamine compound selected from polyether diamines having a polytetramethylene oxide (PTMO) skeleton, branched diamines, branched alicyclic diamines, and norbornane diamines, and (C) a certain dicarboxylic acid compound. The diamine compounds used in the invention described in Patent Document 3, however, have insufficient reactivity and require a long period of time for polymerization. This may cause thermal degradation of part of the polymerization product during polymerization, coloration of an elastomer to be obtained, or insufficient progress of the reaction, and thus yielding a problem like insufficient strength like breaking elongation and breaking strength of the obtained elastomer.

Patent Document 4 discloses a polyether polyamide copolymer resin that has a breaking elongation of 1000% or higher and a modulus of elasticity of 15 MPa or lower and is for use in coating of or impregnation into flexible woven fabric. Furthermore, as a specific constitution, a polyether polyamide resin that is obtained by binding between a soft segment consisting of polyether polyamide that is composed of a polyether diamine compound having an alkylene group with carbon atom number of 2 to 3 and a certain dicarboxylic acid compound, and a hard segment consisting of polyamide that is composed of a certain aminocarboxylic acid and/or a certain lactam compound is disclosed. However, the polyether polyamide resin described in Patent Document 4 has a problem that the polyether compound has poor reactivity and the breaking strength of the resin is insufficient.

Patent Document 1: Japanese Unexamined Patent Application, Publication No. S59-193923
Patent Document 2: Japanese Unexamined Patent Application, Publication No. S59-131628
Patent Document 3: PCT International Publication No. WO2007/145324
Patent Document 4: PCT International Publication No. WO2009/139087

DISCLOSURE OF THE INVENTION

Problems to be Solved by the Invention

In consideration of the above problems, an object of the present invention is to provide a polyamide resin having excellent balance of mechanical characteristics such as breaking strength and breaking elongation in a solid state, a molded body containing the polyamide resin, a laminate provided with a film or a sheet containing the polyamide resin, a medical device provided with at least one of the molded body and the laminate, and a method for producing the polyamide resin.

Means for Solving the Problems

The inventors of the present invention conducted intensive studies to solve the problems described above, and, as a result, completed the present invention. Namely, the present invention relates to a polyamide resin according to [1] to [8] below, a molded body of [9] and [10] below, a laminate of [11] below, a medical device of [12] below, and a method for producing a polyamide resin of [13] and [14] below.

[1] A polyamide resin containing a unit (a), a unit (b), a unit (c), and a unit (d),
in which the unit (a) is a unit represented by the following formula (A):

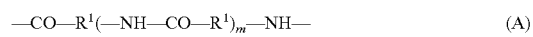

(in the formula (A), $R^1$ is, independently, a linear saturated hydrocarbon group having 6 or more and 18 or less carbon atoms, m is an integer of 0 or more and 100 or less, and, when m is an integer of 1 or more, a plurality of $R^1$ may be the same or different from each other),
the unit (b) is a unit represented by the following formula (B):

(in the formula (B), $R^2$ is a single bond or a linear saturated hydrocarbon group having 1 or more and 20 or less carbon atoms),
the unit (c) is a unit represented by the following formula (C):

$$—NH—(CH(CH_3)CH_2O—)_x—(CH_2CH_2O—)_y—(CH(CH_3)CH_2O—)_z—CH_2CH(CH_3)—NH— \quad (C)$$

(in the formula (C), x+z is an integer of 1 or more and 6 or less and y is an integer of 1 or more and 20 or less), the unit (d) is a unit represented by the following formula (D) and with a structure that is different from the unit (c):

$$—NH—R^3(—O—R^4)_n—NH— \quad (D)$$

(in the formula (D), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other),
a ratio between a mole number X of the unit (c) and a mole number Y of the unit (d) in the polyamide resin is 9/1 to 1/9 in terms of X/Y,
a total content of the unit (a), the unit (b), the unit (c), and the unit (d) in the polyamide resin is 90% by mass or more, and
a ratio between a carbonyl terminal group molar amount (Ac) and an amino terminal group molar amount (Aa) in whole units constituting the polyamide resin is 80/100 to 100/80 in terms of Ac/Aa.

[2] The polyamide resin described in [1], in which the unit (d) is at least one selected from a diamino unit having an integer of 2 or more as n and containing a butane-1,4-diyl group and a propane-1,2-diyl group as $R^4$, and a diamino unit represented by the following formula (d-1):

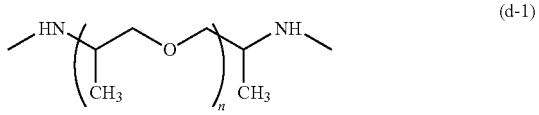

(d-1)

(in the formula (d-1), n is an integer of 1 or more and 8 or less, and number average molecular weight of the diamino unit represented by the formula (d-1) is 500 or less).

[3] The polyamide resin described in [1] or [2], in which a number average molecular weight is 10,000 or more and 150,000 or less.

[4] The polyamide resin described in any one of [1] to [3], in which, when a mole number of the unit (a) is Ma and a mole number of the unit (b) is Mb in whole units constituting the polyamide resin, a ratio Ma/Mb is 95/100 to 100/95.

[5] The polyamide resin described in any one of [1] to [4], in which a content of the unit (a) is 1 to 98.8% by mass, a content of the unit (b) is 1 to 98.8% by mass, a content of the unit (c) is 0.1 to 97.9% by mass, and a content of the unit (d) is 0.1 to 97.9% by mass in the polyamide resin.

[6] The polyamide resin described in any one of [1] to [5], in which a Shore D hardness of the polyamide resin is 60 or more.

[7] The polyamide resin described in any one of [1] to [6], in which a breaking elongation of the polyamide resin is 200% or more.

[8] The polyamide resin described in any one of [1] to [7], in which a breaking stress of the polyamide resin is 30 MPa.

[9] A molded body formed of a material containing the polyamide resin described in any one of [1] to [8].

[10] The molded body described in [9], in which the molded body is a film, a sheet, a tube, a powder, a fiber, a woven fabric, a non-woven fabric, or a catheter balloon.

[11] A laminate containing the film or the sheet described in [10].

[12] A medical device provided with at least one selected from the group consisting of the molded body described in [10] and the laminate described in [11].

[13] A method for producing the polyamide resin described in any one of [1] to [8] including (i) reacting aminocarboxylic acid (a1) represented by the following formula (A1):

$$HOOC—R^1(—NH—CO—R^1)_m—NH_2 \quad (A1)$$

(in the formula (A1), $R^1$ is, independently, a linear saturated hydrocarbon group having 6 or more and 18 or less carbon atoms, m is an integer of 0 or more and 100 or less, and, when m is an integer of 1 or more, a plurality of $R^1$ may be the same or different from each other),
or an amide-forming derivative thereof with dicarboxylic acid (b1) represented by the following formula (B1):

$$HOOC—R^2—COOH \quad (B1)$$

(in the formula (B1), $R^2$ is a single bond or a linear saturated hydrocarbon group having 1 or more and 20 or less carbon atoms),
or an amide-forming derivative thereof to obtain a prepolymer, and
(ii) reacting the prepolymer with diamine (c1) represented by the following formula (C1):

$$H_2N—(CH(CH_3)CH_2O—)_x—(CH_2CH_2O—)_y—(CH(CH_3)CH_2O—)_z—CH_2CH(CH_3)—NH_2 \quad (C1)$$

(in the formula (C1), x+z is an integer of 1 or more and y is an integer of 1 or more and 20 or less),
and diamine (d1) represented by the following formula (D1) and having a structure that is different from the unit (c1) to produce a polyamide resin:

$$H_2N—R^3(—O—R^4)_n—NH_2 \quad (D1)$$

(in the formula (D1), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other).

[14] The method described in [13], in which the reaction for producing a prepolymer and the reaction for producing a polyamide resin are carried out by a melt kneading method.

Effects of the Invention

According to the present invention, a polyamide resin having excellent balance of mechanical characteristics such as breaking strength and breaking elongation in a solid state, a molded body containing the polyamide resin, a laminate provided with a film or a sheet containing the polyamide resin, a medical device provided with at least one of the molded body and the laminate, and a method for producing the polyamide resin can be provided.

PREFERRED MODE FOR CARRYING OUT THE INVENTION

<<Polyamide Resin>>

The polyamide resin contains the unit (a), the unit (b), the unit (c), and the unit (d). Each unit will be described later in detail. In the polyamide resin, ratio between mole number X of the unit (c) and mole number Y of the unit (d) is 9/1 to 1/9 in terms of X/Y.

Total content of the unit (a), the unit (b), the unit (c), and the unit (d) in the polyamide resin is 90% by mass or more, preferably 95% by mass or more, more preferably 98% by mass or more, and particularly preferably 100% by mass. As long as the polyamide resin contains a prescribed kind of the unit (a) in a prescribed amount, it may also contain, in a small amount, an ester bond, (—CO—O—), a urethane bond (—NH—CO—O—), and a carbonate bond (—O—CO—O—), or the like.

From the viewpoint of having various favorable mechanical characteristics, the polyamide resin preferably contains the unit (a), the unit (b), the unit (c), and the unit (d), and it is preferably composed of the unit (a), the unit (b), the unit (c), and the unit (d).

In the whole units constituting the polyamide resin, ratio between the carbonyl terminal group molar amount (Ac) and the amino terminal group molar amount (Aa) is, in terms of Ac/Aa, 80/100 to 100/80, preferably 90/100 to 100/90, more preferably 95/100 to 100/95, and particularly preferably 100/100.

The polyamide resin satisfying the above prescribed requirements exhibits elastomeric characteristics, and it is suitably used as a polyamide elastomer.

Hereinbelow, each unit to be contained in the polyamide resin is explained.

<Unit (a)>

The unit (a) is a unit represented by the following formula (A):

—CO—R$^1$(—NH—CO—R$^1$)$_m$—NH—     (A)

(in the formula (A), R$^1$ is, independently, a linear saturated hydrocarbon group having 6 or more and 18 or less carbon atoms, m is an integer of 0 or more and 100 or less, and, when m is an integer of 1 or more, a plurality of R$^1$ may be the same or different from each other).

In the formula (A), R$^1$ is, each independently, a linear saturated hydrocarbon group having 6 or more and 18 or less carbon atoms. From the viewpoint of easily obtaining a polyamide resin with favorable mechanical characteristics, carbon atom number of R$^1$ is 6 or more and 18 or less, preferably 8 or more and 16 or less, and more preferably 10 or more and 14 or less. Furthermore, the unit (a) has a function of a hard segment in the polyamide resin. In addition, the toughness of the polyamide resin tends to be enhanced as the carbon atom number of R$^1$ increases.

Specific examples of R$^1$ include a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, and an octadecane-1,18-diyl group.

The value of m is, within a range in which the object of the present invention is not inhibited, not particularly limited in a range of 0 or more and 100 or less. From the viewpoint of polymerization reactivity and favorable dynamic characteristics of a polyamide resin to be obtained, m is preferably 1 or more and 100 or less, more preferably 10 or more and 50 or less, and particularly preferably 20 or more and 40 or less. The unit (a) contains, in general, various units having different value of m. Mean value of m can be determined by number average molecular weight that is determined by gel permeation chromatography (GPC).

In a case in which m is 0, specific examples of a suitable monomer to give the unit (a) include 6-aminohexanoic acid, 7-aminoheptanoic acid, 8-aminooctanoic acid, 9-aminononanoic acid, 10-aminodecanoic acid, 11-aminoundecanoic acid, 12-aminododecanoic acid, 13-aminotridecanoic acid, 14-aminotetradecanoic acid, 15-aminopentadecanoic acid, 16-aminohexadecanoic acid, 17-aminoheptadecanoic acid, 18-aminooctadecanoic acid, and 19-aminononadecanoic acid. In a case in which m is 1 or more and 100 or less, the monomer to give the unit (a) is obtained by condensing a prescribed amount of the above aminoalkanoic acid. In that case, it is also possible to obtain a monomer in which m is 1 or more by condensing aminoalkanoic acids of different types.

Content of the unit (a) in the polyamide resin is, from the viewpoint of easily obtaining a polyamide resin with favorable mechanical characteristics, preferably 1 to 99% by mass, more preferably 1 to 98.8% by mass, even more preferably 50 to 99% by mass, and particularly preferably 70 to 99% by mass.

Furthermore, when the mole number of the unit (a) is Ma and the mole number of the unit (b) is Mb in whole units constituting the polyamide resin, it is preferable that ratio Ma/Mb is 95/100 to 100/95. The polyamide resin preferably contains a dicarbonyl unit derived from a prepolymer consisting of a complex unit in which the unit (b) binds to the amino group terminal of the unit (a). As the ratio Ma/Mb is within the above range, the dicarbonyl unit derived from a prepolymer with desired structure is produced favorably.

<Unit (b)>

The unit (b) is a unit represented by the following formula (B):

—CO—R$^2$—CO—     (B)

(in the formula (B), R$^2$ is a single bond or a linear saturated hydrocarbon group having 1 or more and 20 or less carbon atoms).

R$^2$ in the formula (B) is a single bond or a linear saturated hydrocarbon group having 1 or more and 20 or less carbon atoms. From the viewpoint of easily obtaining a polyamide resin with favorable mechanical characteristics, carbon atom number of R$^2$ is 1 or more and 20 or less, preferably 2 or more and 20 or less, more preferably 4 or more and 12 or less, and particularly preferably 6 or more and 10 or less. In addition, the toughness of the polyamide resin tends to be enhanced as the carbon atom number of R$^2$ increases.

Specific examples of suitable R$^2$ include a methylene group, an ethane-1,2-diyl group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, and a decane-1,10-diyl group.

Specific examples of a suitable monomer to yield the unit (b) include succinic acid, glutaric acid, adipic acid, pimelic acid, suberic acid, azelaic acid, sebacic acid, undecane diacid, and dodecane diacid.

Content of the unit (b) in the polyamide resin is, from the viewpoint of easily obtaining a polyamide resin with favorable mechanical characteristics, preferably 1 to 99% by mass, more preferably 1 to 98.8% by mass, even more preferably 1 to 50% by mass, particularly preferably 1 to 10% by mass, and most preferably 1 to 5% by mass.

<Unit (c)>

The unit (c) is a unit represented by the following formula (C):

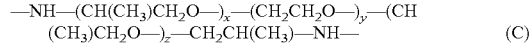

—NH—(CH(CH$_3$)CH$_2$O—)$_x$—(CH$_2$CH$_2$O—)$_y$—(CH(CH$_3$)CH$_2$O—)$_z$—CH$_2$CH(CH$_3$)—NH—     (C)

(in the formula (C), x+z is an integer of 1 or more and 6 or less and y is an integer of 1 or more and 20 or less).

With regard to x, y and z in the formula (C), x+z is a real number of 1 or more and 6 or less and y is a real number of 1 or more and 20 or less. Accordingly, suitable balance of polymerization reactivity and flexibility can be obtained. x+z is preferably 1 or more and 5 or less, and more preferably 1 or more and 3.8 or less. Furthermore, y is preferably 1 or more and 15 or less, and more preferably 1 or more and 9.2 or less. Furthermore, it is preferable that x+z is a real number of 1 or more and 6 or less and y is a real number of 1 or more and 15 or less. Herein, x, y, and z may be determined by GPC measurement as described, for example, in examples below.

Examples of a monomer compound to give the unit (c) include a polyether diamine compound that is an amino-modified form of polyoxyalkylene like polyoxyethylene, 1,2-polyoxypropylene, 1,3-polyoxypropylene, or a copolymer thereof. Specifically, Jeffamine ED series manufactured by HUNTSMAN Corporation, USA can be preferably used, for example. As Jeffamine ED series in which x+z of 1 is more and 6 or less and y is 1 or more and 20 or less in the formula (C), there are ED600 and ED900. Among them, ED900 has (x+z) of 1 or more and 6 or less, ED600 has (x+z) of 1 or more and 3.8 or less, ED900 has y of 1 or more and 15 or less, and ED600 has y of 1 or more and 9.2 or less. Furthermore, among those in which x+z and y are within the aforementioned range, number average molecular weights of ED600 is preferably 500 to 700 and number average molecular weights of ED900 is preferably 800 to 1000. The number average molecular weight for this case is the numerical value calculated from the proton ratio that is obtained by nuclear magnetic resonance using chloroform solvent.

Molecular weight of a monomer compound to give the unit (c) is, from the viewpoint of easily obtaining a polyamide resin with excellent balance of mechanical characteristics such as breaking strength and breaking elongation and also with desired molecular weight, preferably 100 or more and 1,000 or less.

Content of the unit (c) in the polyamide resin is preferably 0.1 to 99.9% by mass, more preferably 1 to 99% by mass, even more preferably 1 to 97.9% by mass, particularly preferably 1 to 30% by mass, and most preferably 1 to 20% by mass. Furthermore, in the polyamide resin, ratio between mole number X of the unit (c) and mole number Y of the unit (d) is 9/1 to 1/9 in terms of X/Y.

<Unit (d)>

The unit (d) is a unit that is represented by the following formula (D):

(in the formula (D), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other),
and has a structure that is different from the unit (c).

In the formula (D), $R^3$ and $R^4$ are a chain aliphatic group having 1 or more and 6 or less carbon atoms. From the viewpoint of easily obtaining a polyamide resin with favorable mechanical characteristics, carbon atom number of $R^3$ and $R^4$ is 1 or more and 6 or less, and preferably 2 or more and 4 or less for each.

Specific examples of suitable $R^5$ and $R^6$ include a methane group, an ethane-1,2-diyl group, an ethane-1,1-diyl group, a propane-1,3-diyl group, a propane-1,2-diyl group, a propane-1,1-diyl group, a propane-2,2-diyl group, a butane-1,4-diyl group, a pentane-1,5-diyl group, and a hexane-1,6-diyl group. Among them, an ethane-1,2-diyl group, a propane-1,3-diyl group, a propane-1,2-diyl group, and a butane-1,4-diyl group are preferable, and an ethane-1,2-diyl group and a propane-1,2-diyl group are more preferable.

The unit (d) is preferably at least one selected from a diamino unit having an integer of 2 or more as n and 20 or less and containing a butane-1,4-diyl group and a propane-1,2-diyl group as $R^4$, and a diamino unit represented by the following formula (d-1):

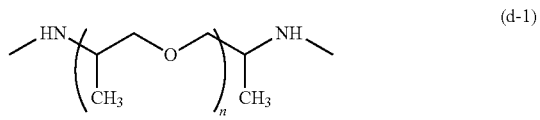

(in the formula (d-1), n is an integer of 1 or more and 8 or less, and number average molecular weight of the diamino unit represented by the formula (d-1) is 500 or less).

Molecular weight of a monomer to give the unit (d) is, from the viewpoint of easily obtaining a polyamide resin with excellent balance of mechanical characteristics such as breaking strength and breaking elongation and also with desired molecular weight, preferably 100 or more and 1,000 or less. n in the formula (D) is suitably selected such that the molecular weight of the monomer to give the unit (d) has a desired value.

Content of the unit (d) in the polyamide resin is preferably 0.1 to 99.9% by mass, more preferably 1 to 99% by mass, even more preferably 1 to 97.9% by mass, and particularly preferably 1 to 30% by mass. Furthermore, in the polyamide resin, ratio between mole number X of the unit (c) and mole number Y of the unit (d) in the polyamide resin is 9/1 to 1/9 in terms of X/Y.

As for the content of each unit described above in the polyamide resin, it is preferable that content of the unit (a) is 1 to 98.8% by mass, content of the unit (b) is 1 to 98.8% by mass, content of the unit (c) is 0.1 to 97.9% by mass, and content of the unit (d) is 0.1 to 97.9% by mass.

<Other Components>

The polyamide resin described above may contain a phosphorus compound. Accordingly, the breaking elongation or the breaking stress of a molded body containing the polyamide resin may be further enhanced. Due to this reason, the polyamide resin composition containing a phosphorus compound is suitable for a balloon for medical use, for example. In addition, coloration caused by stabilization of the polymerization reaction or by oxidation during production process of the polyamide resin may be prevented, as described below. Examples of the phosphorus compound include phosphoric acid, pyrophosphoric acid, polyphosphoric acid, phosphorous acid, hypophosphorous acid, and alkali metal salts and alkaline-earth metal salts thereof. Among them, phosphorous acid, hypophosphorous acid, and alkali metal salts and alkaline-earth metal salts thereof are preferable from the viewpoint of enhancing polymerization reaction stability, imparting thermal stability to the polyamide resin, and enhancing the dynamic characteristics of the molded body. Content of the phosphorus compound is, in terms of phosphorus atom, preferably 5 ppm by mass or more and 5000 ppm by mass or less, more preferably 20 ppm by mass or more and 4000 ppm by mass or less, and even more preferably 30 ppm by mass or more and 3000 ppm by mass or less relative to the mass of the polyamide resin.

Other than the phosphorus compounds described above, the polyamide resin may be blended with, in a range in which the characteristics are not impaired, various additives depending on the purpose. Specifically, a heat resistant agent, a ultraviolet absorbing agent, a photostabilizing agent, an anti-oxidizing agent, an anti-static agent, a lubricant, a slip agent, a crystal nucleating agent, an agent for imparting adhesiveness, a release agent, a plasticizer, a pigment, a dye, a flame retardant, a reinforcing agent, an inorganic filler, micro fiber, an x-ray opaque agent or the like may be added.

The polyamide resin can be produced by carrying out, at desire ratio, polycondensation of monomers for giving the above units according to a known method.

It is preferable that the polyamide resin has a melt viscosity (melt flow rate, MFR) ranging from 0.1 to 20 (g/10 min) at 230° C. and 2.16 kgf (21.2 N). Accordingly, favorable extrusion moldability is obtained. To have the melt viscosity within this range, it is preferable to carry out appropriate adjustment of the polymerization reaction temperature, the reaction time, and the concentration of the solution or the like.

A Shore D hardness of the polyamide resin is preferably 50 or more, for example, and it is more preferably 60 or more, and even more preferably 65 or more. More specifically, a Shore D hardness is preferably 50 to 100, more preferably of 60 to 80, and even more preferably 65 to 80. Accordingly, flexibility of the molded body is obtained. The Shore D hardness can be adjusted by appropriate modification of the compositional ratio of a monomer for giving each unit, for example.

Number average molecular weight of the polyamide resin is preferably 10,000 or more and 150,000 or less, and more preferably 20,000 or more and 100,000 or less. With the number average molecular weight being within this range, excellent processability or excellent mechanical characteristic is obtained.

With regard to the polyamide resin, breaking elongation in a tensile test of a molded body is preferably 100% or more, for example, more preferably 200% or more, and even more preferably 350% or more. More specifically, breaking elongation is preferably 100% or more and 600% or less, more preferably of 200% or more and 600% or less, and even more preferably 350% or more and 600% or less. Furthermore, breaking stress is preferably 20 MPa or more, more preferably 30 MPa or more, and even more preferably 65 MPa or more. More specifically, breaking stress is preferably 20 MPa or more and 100 MPa or less, more preferably of 30 MPa or more and 90 MPa or less, and even more preferably 65 MPa or more and 90 MPa or less. In addition, the tensile test is carried out by a method described below, for example.

Because the polyamide resin explained above has excellent balance of mechanical characteristics such as breaking strength and breaking elongation, it is desirably used for various uses.

<<Method for Producing Polyamide Resin>>

The polyamide resin explained above can be produced by reacting a monomer to give the unit (a), a monomer to give the unit (b), a monomer to give the unit (c), and a monomer to give the unit (d). Examples of the reaction method include a method of simultaneously mixing a monomer to give the unit (a), a monomer to give the unit (b), a monomer to give the unit (c), and a monomer to give the unit (d) followed by their reaction, and a method of reacting a monomer to give the unit (a) with a monomer to give the unit (b) and adding remaining monomers thereto to have a reaction.

Between the above reaction methods, from the viewpoint of efficiently synthesizing the polyamide resin as a block copolymer which has a desired hard segment and a desired soft segment, it is preferable to have a method including (i) a step of mixing a monomer to give the unit (a) with a monomer to give the unit (b) and reacting them to obtain a prepolymer (hereinbelow, referred to as "step (i)") and a step of mixing the prepolymer obtained from the step (i) with a monomer to give the unit (c) and a monomer to give the unit (d) and reacting them (hereinbelow, referred to as "step (ii)").

Namely, the polyamide resin explained above is preferably produced by a method including
(i) reacting aminocarboxylic acid (a1) represented by the following formula (A1):

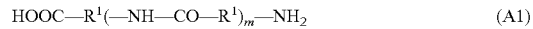

$$HOOC-R^1(-NH-CO-R^1)_m-NH_2 \quad (A1)$$

(in the formula (A1), $R^1$ is, independently, a linear saturated hydrocarbon group having 6 or more and 18 or less carbon atoms, m is an integer of 0 or more and 100 or less, and, when m is an integer of 1 or more, a plurality of R' may be the same or different from each other), or an amide-forming derivative thereof with dicarboxylic acid (b1) represented by the following formula (B1):

$$HOOC-R^2-COOH \quad (B1)$$

(in the formula (B1), $R^2$ is a single bond or a linear saturated hydrocarbon group having 1 or more and 20 or less carbon atoms),
or an amide-forming derivative thereof
to obtain a prepolymer, and
(ii) reacting the prepolymer with diamine (c1) represented by the following formula (C1):

$$H_2N-(CH(CH_3)CH_2O-)_x-(CH_2CH_2O-)_y-(CH(CH_3)CH_2O-)_z-CH_2CH(CH_3)-NH_2 \quad (C1)$$

(in the formula (C1), x+z is an integer of 1 or more, y is an integer of 1 or more and 20 or less, and $R^3$ and $R^4$ are, each independently, a chain aliphatic group having 1 or more and 6 or less carbon atoms),
and diamine (d1) represented by the following formula (D1) and having a structure that is different from the unit (c1) to produce a polyamide resin:

$$H_2N-R^3(-O-R^4)_n-NH_2 \quad (D1)$$

(in the formula (D1), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other).

The aminocarboxylic acid (a1) or an amide-forming derivative thereof is a monomer to give the unit (a) that is described in the above. The dicarboxylic acid (b1) or an amide-forming derivative thereof is a monomer to give the unit (b) that is described in the above. The diamine (c1) is a monomer to give the unit (c) that is described in the above. The diamine (d1) is a monomer to give the unit (d) that is described in the above. Furthermore, examples of the amide-forming derivative include acid halide and lactam. Examples of the acid halide include acid chloride and acid bromide, and acid chloride is preferable.

For synthesizing the polyamide resin, use amount of each monomer is suitably adjusted such that content of each unit has a target value for each. For producing the polyamide resin, addition of a monomer, which may become a cause of disrupting the equimolar property between the amino group and carboxylic group, is suitably carried out to the extent that the desired physical properties are not impaired by it.

For the method for producing a polyamide resin, the polycondensation reaction of monomers in the steps (i) and (ii) may be carried out either in solvent or without using a solvent, i.e., in solvent-free state. For the purpose of easily obtaining a desired polyamide resin without purification or the like, it is preferable that the reaction is carried out without using a solvent, i.e., at solvent-free condition. This reaction at solvent-free condition may be carried out by a melt kneading method. Therefore, it is preferable that, for synthesizing a prepolymer in the step (i) or synthesizing the polyamide resin in the step (ii), the monomers are reacted by a melt kneading method.

For the method for producing a polyamide resin, as a polycondensation reaction, normal-pressure melt polycondensation reaction, reduced-pressure melt polycondensation reaction, or a combination of these may be employed for the polymerization reaction. In the case of reduced-pressure melt polycondensation, it is preferable to set a pressure inside the reaction vessel at 0.1 to 0.01 MPa in a nitrogen gas atmosphere, from the viewpoint of polymerization reactivity. Those melt polycondensation reactions may be carried out by a melt kneading method in a solvent-free state.

The temperature for reacting monomers in the steps (i) and (ii) in the method for producing a polyamide resin is, although not particularly limited as long as it allows an occurrence of the polycondensation reaction, preferably 160 to 300° C., and more preferably from 200 to 280° C. from the viewpoint of the balance between the reaction rate and inhibition of thermal degradation. Furthermore, the reaction temperature in the step (i) may be the same as or different from the reaction temperature in the step (ii).

The polycondensation reaction time of the steps (i) and (ii) in the method for producing a polyamide resin is, from the viewpoint of having high molecular weight for the molecular weight, inhibiting coloration, or the like, preferably 3 to 10 hours. Furthermore, the polycondensation reaction time of the steps (i) and (ii) may be the same or different from each other.

The method for producing a polyamide resin may be carried out either in a batch mode or in a continuous mode. For example, any of the following may be adopted: a batch mode that is carried out in a batch-mode reaction tank or the like; and a continuous mode that is carried out in a single-tank or multi-tank continuous reaction apparatus, a tubular-shape continuous reaction apparatus, or a combination of these apparatuses.

In the production of the polyamide resin, if necessary, a phosphorus compound may be used as a catalyst. Examples of the phosphorus compound include phosphoric acid, pyrophosphoric acid, polyphosphoric acid, phosphorous acid, hypophosphorous acid, and alkali metal salts and alkaline-earth metal salts thereof. Among them, an inorganic phosphorus compound such as phosphorous acid, hypophosphorous acid, and alkali metal salts and alkaline-earth metal salts thereof is preferably used from the viewpoint of enhancing polymerization reaction stability, imparting thermal stability to the polyamide resin, and enhancing the dynamic characteristics of a molded body. It is preferable that weight of the phosphorus compounds at the time of their addition is, in at least one of the steps (i) and (ii), 10 ppm by mass or more and 10000 ppm by mass or less, and more preferably 100 ppm by mass or more and 5000 ppm by mass or less relative to the total weight of the monomers. Furthermore, because there is also a case in which the phosphorus compound is released to the outside of the reaction system as caused by a reaction by-product that is generated during the reaction, the amount of the phosphorus compound added may not be necessarily equivalent to the content of the phosphorus element in the polyamide resin. It is preferable to contain the phosphorus element such that content thereof in the polyamide resin is 5 ppm by mass or more and 5000 ppm by mass or less, more preferably 20 ppm by mass or more and 4000 ppm by mass or less, and even more preferably 30 ppm by mass or more and 3000 ppm by mass or less.

After the reaction of each component in the step (ii) is completed, the polymer in molten state may be extruded in a strip shape followed by cooling, and, if necessary, obtained as pellet or the like, for example.

<<Molded Body>>

As described in the above, the polyamide resin has excellent balance of mechanical characteristics such as breaking strength and breaking elongation. As such, the molded body composed of this polyamide resin, or the molded body composed of this polyamide resin having various additives blended therein is suitably used for various uses.

Shape of the molded body or the like is not particularly limited. The polyamide resin and composition of the polyamide resin are processed into molded articles in various forms by various known molding methods, spinning method, a method for producing fabric, or the like. As for the molding method, extrusion molding, blow molding, injection molding, or the like can be applied. Examples of a suitable shape of the molded body include a film, a sheet, a tube, a powder, a fiber, a woven fabric, a non-woven fabric, and a catheter balloon.

From the viewpoint of that the polyamide resin and polyamide resin composition have excellent breaking strength or breaking elongation, the molded body composed of the polyamide resin or the polyamide resin composition is preferably a film, a sheet, or a tube, for example. As the film or sheet composed of the polyamide resin or the polyamide resin composition is included in a laminate, favorable breaking strength or breaking elongation is given also to the laminate. Due to this reason, a laminate containing the film or sheet composed of the polyamide resin or the polyamide resin composition is also preferable.

The polyamide resin described above has excellent extrusion moldability and excellent drawing moldability resulting from the melt characteristics of the resin, and also excellent blow moldability and excellent strength and toughness. Thus, it can be used for producing molded articles in various fields. For example, the polyamide resin may be used for extrusion molding for production of a member such as a tube, a hose, and a medical tube. Furthermore, the polyamide resin may be subjected to blow molding to produce a member like a bottle, a container, a catheter balloon, and the like. In particular, the polyamide resin is suitable as a constitutional material of a medical member that is used in a medical device. Examples of the medical member include a catheter balloon, a medical tube, and a laminate.

Hereinbelow, the medical member made by using the polyamide resin is described by referring to a case in which the medical member is a catheter balloon, but the molded body used as a medical member is not limited thereto.

A catheter balloon (hereinbelow, simply referred to as "balloon") can be produced by preparing first a tube (hereinbelow, simply referred to as "parison") using the polyamide resin and further processing thus-obtained parison. As a method of preparing a parison using the polyamide resin, a generally known molding method can be used. Examples of the method include extrusion molding, injection molding, and melt spinning molding. The parison shape is, in general, a cylinder shape with a diameter which remains constant in the long-axis direction. As for the method of preparing a balloon from the parison, a generally known molding method may be used. For example, a blow molding method such as free blowing or mold blowing or a vacuum molding method may be employed to carry out biaxial stretching molding to prepare a balloon with a desired shape. The molding temperature is from 95 to 165° C. in general. It is preferable that the enlargement rate of the inner diameter of a balloon from the parison is preferably 400% or more and 900% or less, and more preferably 500% or more and 800% or less. Furthermore, the enlargement rate of the inner diameter in the present invention is calculated by the following equation.

Enlargement rate of inner diameter (%)=(Inner diameter at balloon inflation during molding)/(Inner diameter of parison)×100

The balloon prepared as described in the above is subjected to examinations such as outer appearance examination or the like, and only after it has passed the examinations, the balloon is eligible to be used as a medical member for use in a medical device such as a balloon catheter. When a diamond-shaped dent or a fish eye, or a crack is observed from a surface of the balloon according to an outer appearance examination, the balloon is regarded as an inferior product.

As described in the above, since the polyamide resin has excellent balance of dynamic characteristics such as breaking elongation or breaking strength, the polyamide resin can be used, other than a member for medical device, for various uses including a packaging material for food and the like, a member for an electric/precision machine device, a member for an automobile or the like.

EXAMPLES

Hereinbelow, explanations are given in view of specific examples to further clearly describe the present invention, but the present invention is not limited to them.

Hereinbelow, with regard to evaluation of the polyamide resin of Examples and Comparative Examples, the method for tensile test and method for measuring a Shore D hardness are explained.

(Tensile Test)

A tensile test was carried out using a test specimen that was compliant with ASTM-D638 (TYPE5). The test specimen was prepared as follows: a pellet of a polyamide resin obtained in Examples or Comparative Examples was pressed with a Mini Test Press (manufactured by Toyo Seiki Seisaku-sho, Ltd.; trade name, MP-2FH) at 190° C., and then cooled to prepare a film with a thickness of 1 mm, which was then subjected to blanking with a blanking blade that is compliant with the above specification. The drying treatment of the test specimen was at 80° C. for 4 hours. The tensile test was carried out at a rate of 200 mm/min.

(Measurement of Shore D Hardness)

A sheet with a thickness of 6 mm was subjected to Shore D hardness measurement in accordance with ASTM-D2240 in a thermostatic chamber controlled at 23° C. A sheet with a thickness of 6 mm was prepared from a pellet of the polyamide resin obtained in Examples or Comparative Examples and by using the same press machine as above. As a measurement device, a load tester for D type durometer for rubber manufactured by Kobunshi Keiki Co., Ltd. was used.

Example 1

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 5000 so as to obtain the aminocarboxylic acid (a1) to be a hard segment.

Subsequently, to the reaction vessel, adipic acid as dicarboxylic acid (b1) was added in the same molar amount (0.24 mol, 35 g) as the molar amount of the terminal amine group of the aminocarboxylic acid (a1). According to a reaction between the aminocarboxylic acid (a1) and the dicarboxylic acid (b1) at 220° C. for 1 hour, a prepolymer was obtained (step (i)).

To the reaction vessel, 72 g (about 0.12 mol) of polyether diamine as the diamine (c1) (i.e., diamine represented by the following formula (2), in the formula (2), y=9 and x+z=3.6, Jeffamine ED600 manufactured by HUNTSMAN) and 27.6 g (about 0.12 mol) of polypropylene ether diamine as the diamine (d1) (average repeat number of propylene oxy unit: 2.5, Jeffamine D230 manufactured by HUNTSMAN) were added. By performing polycondensation of the prepolymer, the diamine (c1), and the diamine (d1) at 260° C. for 4 hours, the polyamide resin was obtained (step (ii)).

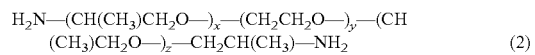

$$H_2N-(CH(CH_3)CH_2O-)_x-(CH_2CH_2O-)_y-(CH(CH_3)CH_2O-)_z-CH_2CH(CH_3)-NH_2 \quad (2)$$

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, measurements of the tensile test and Shore D hardness were carried out. Results of those evaluations are shown in Table 1.

Example 2

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 5200 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amine group of the aminocarboxylic acid (a1). According to a reaction between the aminocarboxylic acid (a1) and the dicarboxylic acid (b1) at 220° C. for 1 hour, a prepolymer was obtained (step (i)).

To the reaction vessel, 72 g (about 0.12 mol) of polyether diamine as the diamine (c1) (Jeffamine ED600 manufactured by HUNTSMAN) and 48 g (about 0.12 mol) of polypropylene ether diamine as the diamine (d1) (average repeat number of propylene oxy unit: 6.1, Jeffamine D400 manufactured by HUNTSMAN) were added. By performing polycondensation of the prepolymer, the diamine (c1), and the diamine (d1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, measurements of the tensile test and Shore D hardness were carried out. Results of those evaluations are shown in Table 1.

Example 3

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 5400 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amine group of the aminocarboxylic acid (a1). According to a reaction between the aminocarboxylic acid (a1) and the dicarboxylic acid (b1) at 220° C. for 1 hour, a prepolymer was obtained (step (i)).

To the reaction vessel, 72 g (about 0.12 mol) of polyether diamine as the diamine (c1) (Jeffamine ED600 manufactured by HUNTSMAN) and 17.76 g (about 0.12 mol) of polyether diamine containing a tetramethylene oxy repeating unit and a propylene oxy repeating unit as the diamine (d1) (number average molecular weight: about 148, Jeffamine EDR148 manufactured by HUNTSMAN) were added. By performing polycondensation of the prepolymer, the diamine (c1), and the diamine (d1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, measurements of the tensile test and Shore D hardness were carried out. Results of those evaluations are shown in Table 1.

Comparative Example 1

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 5100 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amine group of the aminocarboxylic acid (a1). According to a reaction between the aminocarboxylic acid (a1) and the dicarboxylic acid (b1) at 220° C. for 1 hour, a prepolymer was obtained (step (i)).

To the reaction vessel, 55.2 g (about 0.24 mol) of polypropylene ether diamine as the diamine (d1) (Jeffamine D230 manufactured by HUNTSMAN) were added. By performing polycondensation of the prepolymer, the diamine (c1), and the diamine (d1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, measurements of the tensile test and Shore D hardness were carried out. Results of those evaluations are shown in Table 1.

Comparative Example 2

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 4900 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amine group of the aminocarboxylic acid (a1). According to a reaction between the aminocarboxylic acid (a1) and the dicarboxylic acid (b1) at 220° C. for 1 hour, a prepolymer was obtained (step (i)).

To the reaction vessel, 96 g (about 0.24 mol) of polypropylene ether diamine as the diamine (d1) (Jeffamine D400 manufactured by HUNTSMAN) were added. By performing polycondensation of the prepolymer and the diamine (d1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, tensile test and Shore D hardness measurement were carried out. Results of those evaluations are shown in Table 1.

Comparative Example 3

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and a polymerization reaction was allowed to proceed until the number average molecular weight reached 4900 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amino group of the aminocarboxylic acid (a1). By reacting the aminocarboxylic acid (a1) and the dicarboxylic acid (b1) at 220° C. for 1 hour, a prepolymer was obtained (step (i)).

To the reaction vessel, 144 g (about 0.24 mol) of polyether diamine as the diamine (c1) (Jeffamine ED600 manufactured by HUNTSMAN) were added. By performing polycondensation of the prepolymer and the diamine (c1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, tensile test and Shore D hardness measurement were carried out. Results of those evaluations are shown in Table 1.

Comparative Example 4

To a 3 L reaction vessel equipped with a stirrer, a temperature controller, a pressure gauge, a nitrogen gas inlet, and a port for discharging the condensate, 1200 g of 12-aminododecanoic acid and 0.6 g of hypophosphorous acid were added. The inside of the reaction vessel was sufficiently replaced with nitrogen, and then, in order to melt the monomers, the temperature was raised to 280° C. for 1 hour and polymerization reaction was allowed to proceed until the number average molecular weight reached 4900 so as to obtain the aminocarboxylic acid (a1) to be a hard segment.

Subsequently, to the reaction vessel, adipic acid as the dicarboxylic acid (b1) was added in the same molar amount (0.24 mol, 35 g) as the molar amount of the terminal amino group of the aminocarboxylic acid (a1). By reacting the aminocarboxylic acid (a1) and the dicarboxylic acid (b1) at 220° C. for 1 hour, a prepolymer was obtained (step (i)).

To the reaction vessel, 240 g (about 0.24 mol) of polyether diamine containing a tetramethylene oxy repeating unit and a propylene oxy repeating unit as the diamine (d1) (Jeffamine THF100 manufactured by HUNTSMAN) were added. By performing polycondensation of the prepolymer and the diamine (d1) at 260° C. for 4 hours, the polyamide resin was obtained (step (ii)).

After the completion of the polymerization, stirring was terminated and then the colorless transparent polyamide resin in a molten state was pulled out, in string shape, through a discharge port, and, after cooling in water, it was pelletized to obtain about 1 kg of pellets. Furthermore, by using the obtained pellets and following the aforementioned method, measurements of the tensile test and Shore D hardness were carried out. Results of those evaluations are shown in Table 1.

TABLE 1

|  | Breaking elongation (%) | Breaking strength (MPa) | Shore D hardness |
|---|---|---|---|
| Ex. 1 | 370 | 75 | 69 |
| Ex. 2 | 420 | 69 | 67 |
| Ex. 3 | 380 | 75 | 69 |
| Comp. Ex. 1 | 270 | 60 | 74 |
| Comp. Ex. 2 | 320 | 71 | 73 |
| Comp. Ex. 3 | 382 | 60 | 68 |
| Comp. Ex. 4 | 322 | 56 | 64 |

According to Table 1, it is recognized that the polyamide resin of Examples containing the unit (a), the unit (b), the unit (c), and the unit (d), each having a prescribed structure and obtained by polycondensation of the aminocarboxylic acid (a1), the dicarboxylic acid (b1), the diamine (c1), and the diamine (d1), each having prescribed structure, has excellent breaking elongation or breaking strength compared to the polyamide resin of Comparative Examples in which one of the unit (c) and the unit (d) is not contained. The polyamide resin of Examples can be particularly preferably used for production of a tube or a balloon for medical use.

The invention claimed is:

1. A polyamide resin, comprising:
a unit (a);
a unit (b);
a unit (c); and
a unit (d),
wherein the unit (a) is a unit represented by the following formula (A):

$$-CO-R^1(-NH-CO-R^1)_m-NH- \quad (A)$$

wherein in the formula (A), $R^1$ is, independently, a linear saturated hydrocarbon group having 6 or more and 18 or less carbon atoms, m is an integer of 0 or more and 100 or less, and, when m is an integer of 1 or more, a plurality of $R^1$ may be the same or different from each other, wherein the unit (b) is a unit represented by the following formula (B):

$$-CO-R^2-CO- \quad (B)$$

wherein in the formula (B), $R^2$ is a single bond or a linear saturated hydrocarbon group having 1 or more and 20 or less carbon atoms, wherein the unit (c) is a unit represented by the following formula (C):

$$-NH-(CH(CH_3)CH_2O-)_x-(CH_2CH_2O-)_y-(CH(CH_3)CH_2O-)_z-CH_2CH(CH_3)-NH- \quad (C)$$

wherein in the formula (C), x+z is an integer of 1 or more and 6 or less and y is an integer of 1 or more and 20 or less, wherein the unit (d) is a unit represented by the following formula (D) and with a structure that is different from the unit (c):

$$-NH-R^3(-O-R^4)_n-NH- \quad (D)$$

wherein in the formula (D), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other, wherein a ratio between a mole number X of the unit (c) and a mole number Y of the unit (d) in the polyamide resin is 9/1 to 1/9 in terms of X/Y, wherein a total content of the unit (a), the unit (b), the unit (c), and the unit (d) in the polyamide resin is 90% by mass or more, wherein a ratio between carbonyl terminal group molar amount (Ac) and amino terminal group molar amount (Aa) in whole units constituting the polyamide resin is 80/100 to 100/80 in terms of Ac/Aa, and wherein a content of the unit (a) is 50 to 99% by mass in the polyamide resin.

2. The polyamide resin according to claim 1, wherein the unit (d) is at least one selected from a diamino unit having an integer of 2 or more as n and containing a butane-1,4-diyl group and a propane-1,2-diyl group as $R^4$, and a diamino unit represented by the following formula (d-1):

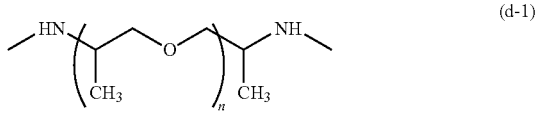

wherein in the formula (d-1), n is an integer of 1 or more and 8 or less, and number average molecular weight of the diamino unit represented by the formula (d-1) is 500 or less.

3. The polyamide resin according to claim 1, wherein a number average molecular weight is 10,000 or more and 150,000 or less.

4. The polyamide resin according to claim 1, wherein, when a mole number of the unit (a) is Ma and when a mole number of the unit (b) is Mb in whole units constituting the polyamide resin, a ratio Ma/Mb is 95/100 to 100/95.

5. The polyamide resin according to claim 1, wherein a Shore D hardness of the polyamide resin is 60 or more.

6. The polyamide resin according to claim 1, wherein a breaking elongation of the polyamide resin is 200% or more.

7. The polyamide resin according to claim 1, wherein a breaking stress of the polyamide resin is 30 MPa or more.

8. A molded body formed of a material comprising the polyamide resin according to claim 1.

9. The molded body according to claim 8, wherein the molded body is a film, a sheet, a tube, a powder, a fiber, a woven fabric, a non-woven fabric, or a catheter balloon.

10. A laminate comprising the molded body according to claim 9, wherein the molded body is a film or a sheet.

11. A medical device comprising the molded body according to claim 9.

12. A method for producing the polyamide resin according to claim 1 comprising:

(i) reacting aminocarboxylic acid (a1) represented by the following formula (A1):

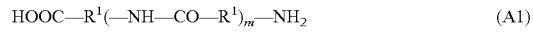

wherein in the formula (A1), $R^1$ is, independently, a linear saturated hydrocarbon group having 6 or more and 18 or less carbon atoms, m is an integer of 0 or more and 100 or less, and, when m is an integer of 1 or more, a plurality of $R^1$ may be the same or different from each other, or an amide-forming derivative thereof with dicarboxylic acid (b1) represented by the following formula (B1):

wherein in the formula (B1), $R^2$ is a single bond or a linear saturated hydrocarbon group having 1 or more and 20 or less carbon atoms, or an amide-forming derivative thereof to obtain a prepolymer, and (ii) reacting the prepolymer with diamine (c1) represented by the following formula (C1):

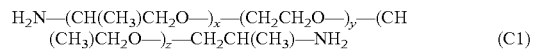

wherein in the formula (C1), x+z is an integer of 1 or more and 6 or less and y is an integer of 1 or more and 20 or less, and diamine (d1) represented by the following formula (D1) and having a structure that is different from the unit (c1) to produce a polyamide resin:

wherein in the formula (D1), $R^3$ and $R^4$ are, each independently, a chain aliphatic group having 1 or more and 6 or less carbon atoms, n is an integer of 1 or more and 20 or less, and, when n is an integer of 2 or more, a plurality of $R^4$ may be the same or different from each other.

13. The method according to claim 12, wherein the reaction for producing a prepolymer and the reaction for producing a polyamide resin are carried out by a melt kneading method.

14. A medical device comprising the laminate according to claim 10.

* * * * *